US005539800A

United States Patent [19]
Katsevich et al.

[11] Patent Number: 5,539,800
[45] Date of Patent: Jul. 23, 1996

[54] PSEUDOLOCAL TOMOGRAPHY

[75] Inventors: Alexander J. Katsevich, Los Alamos, N.M.; Alexander G. Ramm, Manhattan, Kans.

[73] Assignee: The Regents of the University of California, Office of Technology Transfer, Alameda, Calif.

[21] Appl. No.: 410,620

[22] Filed: Mar. 24, 1995

[51] Int. Cl.$^6$ .................................................. G06F 15/00
[52] U.S. Cl. ...................... 378/210; 378/901; 364/413.14
[58] Field of Search .................................... 378/210, 901, 378/4; 364/413.14, 413.16, 413.17, 413.18, 413.19, 413.2

[56] References Cited

U.S. PATENT DOCUMENTS

| | | | |
|---|---|---|---|
| 4,189,775 | 2/1980 | Inouye | 364/414 |
| 4,365,339 | 12/1982 | Pavkovich | 378/15 |
| 4,433,380 | 2/1984 | Abele et al. | 378/901 X |
| 4,446,521 | 5/1984 | Inouye | 364/414 |
| 4,670,892 | 6/1987 | Abele et al. | 378/4 |
| 5,319,551 | 6/1994 | Sekiguchi et al. | 364/413.19 |

OTHER PUBLICATIONS

A. M. Cormack, "Representation of a Function by Its Line Integrals, With Some Radiological Application", 9 Journal of applied Physics, vol. 34, pp. 2722–2727 (Sep. 1963).

R. H. Huesman, "A New Fast Algorithm for the Evaluation of Regions of Interest an Statistical Uncertainty in computed Tomography", 5 Phys. Med. Biol., vol. 29, pp. 543–552 (1984).

Adel Faridani et al., "Local Tomography", 2 Siam J. Appl. Math., vol. 52, pp. 459–484 (Apr. 1992).

Primary Examiner—David P. Porta
Attorney, Agent, or Firm—Ray G. Wilson

[57] ABSTRACT

Local tomographic data is used to determine the location and value of a discontinuity between a first internal density of an object and a second density of a region within the object. A beam of radiation is directed in a predetermined pattern through the region of the object containing the discontinuity. Relative attenuation data of the beam is determined within the predetermined pattern having a first data component that includes attenuation data through the region. The relative attenuation data is input to a pseudo-local tomography function, where the difference between the internal density and the pseudo-local tomography function is computed across the discontinuity. The pseudo-local tomography function outputs the location of the discontinuity and the difference in density between the first density and the second density.

5 Claims, 7 Drawing Sheets

PSEUDOLOCAL TOMOGRAPHY

BACKGROUND OF THE INVENTION

This invention relates to image reconstruction from tomographic data, and, more particularly, to the definition of discontinuity location and size using limited tomographic data. This invention was made with government support under Contract No. W-7405-ENG-36 awarded by the U.S. Department of Energy. The government has certain rights in the invention.

Tomography produces the reconstruction of a generalized density function $f$ from a large number of line integrals of $f$. A practically important objective is the reconstruction, from the x-ray attenutaion data, of functions providing significant information about the physical object, such as the location of discontinuities within an object being interrogated. Tomography equipment for obtaining the attenuation data is well known. For example, in some instances a single source is collimated and traversed across the object, whereby a single sensor output corresponds to a single source transverse location. Here, the source traverses the object at each angular orientation of the object. In other instances, a single source generates a fan-like pattern of radiation that is detected by an array of sensors, where the object is located between the source and the sensor array. The source is then angularly rotated relative to the object to provide a complete set of tomographic data.

Conventional tomography is a global procedure in that the standard convolution formulas for reconstruction of the density at a single point require the line integral data over all lines within some planar cross-section containing the point. Local tomography has been developed for the reconstruction at a point where attenuation data is needed only along lines close to that point within the same cross-section. Local tomography produces the reconstruction of a related function using the square root of the negative Laplace operator and reproduces the locations of discontinuities within an object. See, e.g., E. Vainberg, "Reconstruction of the Internal Three-Dimensional Structure of Objects Based on Real-Time Integral Projections," 17 Sov. J. Nondestr. Test., pp. 415–423 (1981); A. Faridani et al., "Local Tomography," 52 SIAM J. Appl. Math, No. 2, pp. 459–484 (April 1992).

Local tomography can reduce significantly the amount of data needed for the local reconstruction, with a concomitant reduction in x-ray dose. While the location of a discontinuity is reproduced, however, there is no quantitative value for the magnitude of the discontinuity. In many instances it would be useful to know this value, e.g., in order to make medical, technological, or geophysical conclusions.

Accordingly, it is an object of the present invention to determine both the location and size of discontinuities from tomographic data.

It is another object of the present invention to determine the location and size of discontinuities from only limited attenuation data that includes a region containing the discontinuity.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the apparatus of this invention may comprise a method for determining by tomography the location and value of a discontinuity between a first internal density of an object and a second density of a region within the object. A beam of radiation is directed in a predetermined pattern through the region of the object containing the discontinuity. Relative attenuation data of the beam is determined within the predetermined pattern having a first data component that includes attenuation data through the region. The relative attenuation data is input to a pseudo-local tomography function, where the difference between an actual internal density and the pseudo-local tomography function is continuous everywhere and the pseudo-local tomography function is computed across the discontinuity. The pseudo-local tomography function outputs the location of the discontinuity and the difference in density between the first density and the second density.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION OF THE INVENTION

In accordance with the present invention, pseudolocal tomography is used to determine the sizes of density discontinuities within an object, as well as the location of the discontinuity. The determination of these physical characteristics of an object, i.e., discontinuity location and value, is of major interest in many practical applications. For example, medical applications include the location and identification of tumors; technological applications include the identification and analysis of cracks in physical objects, such as aircraft wings; environmental applications include the determination of the location and impact of anomalous waste sites, such as unidentified nuclear waste; geophysical applications include the location and characterization of underground anomalies such as caves and oil deposits.

The density function $f(x)$ is usually reproduced from the line integral data $\hat{f}(\theta,p)$, where $\theta$ is an angle on the unit circle and p is a location of a beam line, by the formula:

$$f(x) = \frac{1}{4\pi^2} \int_{S_1} \int_{-\infty}^{\infty} \frac{\hat{f}(\theta,p)}{x \cdot \Theta - p} \, dp d\theta, \text{ where } x \in \mathfrak{R}^2. \quad \text{Eq. (1)}$$

The present invention defines a pseudolocal tomography (PLT) function $f_{\sigma d}(x)$, where d is the radius of a small disk, $d>0$, centered at a point of reconstruction x, by the formula:

$$f_{\sigma d}(x) = \frac{1}{4\pi^2} \int_{S_1} \int_{x \cdot \Theta - d}^{x \cdot \Theta + d} \frac{\sigma_d(x \cdot \Theta - p)\hat{f}(\theta,p)}{x \cdot \Theta - p} \, dp d\theta, \quad \text{Eq. (2)}$$

where $x \in \mathfrak{R}^2$, $\Theta = (\cos\theta, \sin\theta)$, where the function $\sigma_d(p)$ satisfies the properties that (1) $\sigma_d(p)$ is real-valued, even, and vanishes for $|p| \geq d$;

(2) $\sigma_d(p)$ is piecewise continuously differentiable and there are at most a finite number of points at which $\sigma_d(p)$ is discontinuous, and (3) $\sigma_d(p) = \sigma_1(p/d)$, $|\sigma_d(p) - 1| \leq O(p)$, $p \to 0$.

The function $f_{\sigma d}(x)$ is thus computed at a point x using $\hat{f}(\theta,p)$ for $(\theta,p)$ satisfying $|\Theta \cdot x - p| \leq d$; that is, using integrals of f along only lines passing at a distance not exceeding d from the point x. Since line integrals of f are obtained from measuring attenuation of attenuated radiation, such as x-rays, this means that for the reconstruction of $f_{\sigma d}(x)$ inside a certain region of interest, radiation can be collimated to a domain slightly larger than this region of interest.

It can be shown that (1) the location of discontinuities of $f_{\sigma d}(x)$ is the same as that of f(x), and (2) at each discontinuity point $\xi$ of $f_{\sigma d}$, the jump value $f_{\sigma d}(\xi+0) - f_{\sigma d}(\xi-0)$ is precisely the same as that of f(x) at $x=\xi$.

In a first embodiment of the present invention, let $\sigma_d(p) \equiv 1$; i.e., $f_{\sigma d} = f_{1d} = f_d$. Numerical computation of $f_d$ is done using the standard approach that is widely used for convolution and backprojection-type algorithms, e.g., F. Natterer, *The Mathematics of Computerized Tomography*, J. Wiley & Sons, New York (1986). In place of $f_d$, the function $f_{d\epsilon}$ is computed from Eq. (2) with $\hat{f}$ replaced by $\hat{f}_\epsilon$, where $f_\epsilon$ is the Radon transform of the function $f_\epsilon = f * W_\epsilon$. Here $W_\epsilon$ is a sequence of mollifiers used to smooth (average) f over a small distance $\epsilon$ and that satisfy the following properties:

(a) $W_\epsilon(x)$ is a radial function, $W_\epsilon(x) = W_\epsilon(|\chi|)$;

(b) $W_\epsilon(x) = 0$, $|\chi| \geq \epsilon$; and (c) $W_\epsilon(\chi) = \epsilon^{-2} W_1(\chi/\epsilon)$, $\int_{|\chi| \leq 1} W_1(\chi) d\chi = 1$.

Property (b) is not mandatory for the standard (global) convolution and backprojection algorithms, but is required for the local reconstruction algorithm.

It can be shown that $$f_{d\epsilon}(x) = (f_d * W_\epsilon)(x) \frac{1}{4\pi^2} \int_{S_1} \int_{x \cdot \Theta - d - \epsilon}^{x \cdot \Theta + d + \epsilon} \tilde{w}_\epsilon(x \cdot \Theta - s)\hat{f}(\theta,s) ds d\theta, \quad \text{Eq. (3)}$$

where $$\tilde{w}_\epsilon(s) = \int_{s-d}^{s+d} \frac{w'_\epsilon(p)}{s - p} \, dp, \quad \text{Eq. (4)}$$

and $$w'_\epsilon(p) = 2p \int_p^\epsilon \frac{W_\epsilon(r)}{\sqrt{r^2 - p^2}} \, dr, \quad \text{Eq. (5)}$$

$0 \leq p \leq \epsilon'$, $w'_\epsilon(-p) = -w'_\epsilon(p)$, $p > 0$, $w'_\epsilon(p) = 0, |p| \geq \epsilon$.

Thus, the kernel $\tilde{w}_\epsilon$ is computed first with the above formulas and then the local pseudolocal tomography function $f_{d\epsilon}(x)$ is computed.

The function $f_{d\epsilon}(x)$ is sufficient for obtaining a preliminary image of the discontinuity curve $\Gamma$ of the original object f. The preliminary image is then sharpened by further processing, which also produces the values of the jumps, or discontinuities. This processing is discussed below.

In order to investigate the behavior of $f_{d\epsilon}(x)$ in a neighborhood of $x_0 \in \Gamma$, the coordinate system is changed so that the origin coincides with $x_0$; the $x_1$-axis becomes perpendicular to $\Gamma$ at $x_0$, and the $x_2$-axis becomes tangent to $\Gamma$ at $x_0$. Fix a point $(x'_1, x'_2)$, $x'_1 = \gamma d$, $x'_2 = 0, \gamma \in R$. This point is located at a distance $\gamma d$ from the point $x_0$ and, for different $\gamma$, runs over the line perpendicular to $\Gamma$ at $x_0$. Then, $$f_{d\epsilon}(\gamma d, 0) = D_+(x_0) \int_{\gamma - q}^{\gamma + q} \tilde{W}_q(\gamma - t)\psi(t) dt + O(d^{1/2}) \text{ as} \quad \text{Eq. (6)}$$

$d \to 0, q = \epsilon/d$, where $q, q > 0$, is fixed, $D\pm(x_0) = f\pm(x_0) - f\mp(x_0)$, $$\tilde{W}_1(t) = \epsilon^{-1} \int_{\mathfrak{R}} W_1(t, x_2/\epsilon) dx_2, \tilde{W}_q(t) = \tilde{W}_1(t/q)/q, \text{ and}$$

$$\psi(\gamma) = \frac{2}{\pi^2} \int_0^{\min(1, 1/\gamma)} \frac{\arccos(\gamma t)}{(1-t^2)^{1/2}} \, dt, \gamma > 0.$$

Here, $f\pm(x_0)$ are limiting values of f(x) as f approaches the point $x_0$ at the discontinuity curve $\Gamma$ from different sides. The physical meaning of $D\pm(x_0) = f\pm(x_0) - f\mp(x_0)$ is the value of the density jump. By definition $\psi(-\gamma) = -\psi(\gamma)$, $\gamma > 0$, and note that $\int_R \tilde{W}_q(t) dt = 1$. Then $$\lim_{d \to 0} f_{d\epsilon}(x_o + \gamma d n_+) = D_+(x_o)\psi_q(\gamma), \gamma \in \mathfrak{R}, \quad \text{Eq. (7)}$$

where $\psi_q(\gamma) = \int_{\gamma - q}^{\gamma + q} \tilde{W}_q(\gamma - t)\psi(t) dt$, and $n+$ is the unit normal to $\Gamma$ at the point $x_0$.

Since $\psi(t)$ is a monotonically decreasing function on $(0, \infty)$, $\psi_q(\gamma)$ has a global maximum at a point $\gamma = \gamma_0$, $0 < \gamma_0 \leq q$. Since $\psi_q$ is odd, it has a global minimum at a point $\gamma = -\gamma_0$. Thus, for a sufficiently small d, $f_{d\epsilon}(x_0 + \gamma d n_+)$ as a function of $\gamma$, has a local maximum and minimum at points $\pm\gamma_0$. For each x define $\Phi(x)$ as a difference of values of local maximum of $f_{d\epsilon}$ and a local minimum of $f_{d\epsilon}$ in $\gamma_0 d$ neighborhood of x. The above mentioned properties of $f_{d\epsilon}$ imply that the function $\Phi(x)$ has local maxima (in the direction transversal to $\Gamma$) at the points of $\Gamma$. Moreover, this yields the optimal step size of the grid $h_{opt} \approx \gamma_0 d$, and the jump of the original function f at the point $x_0$ can be computed from $\Phi(x_0)$ by the normalized formula $$|D_+(x_o)| \approx \frac{\Phi(x_o)}{2\psi_q(\gamma_0)}. \quad \text{Eq. (8)}$$

Figure 1:
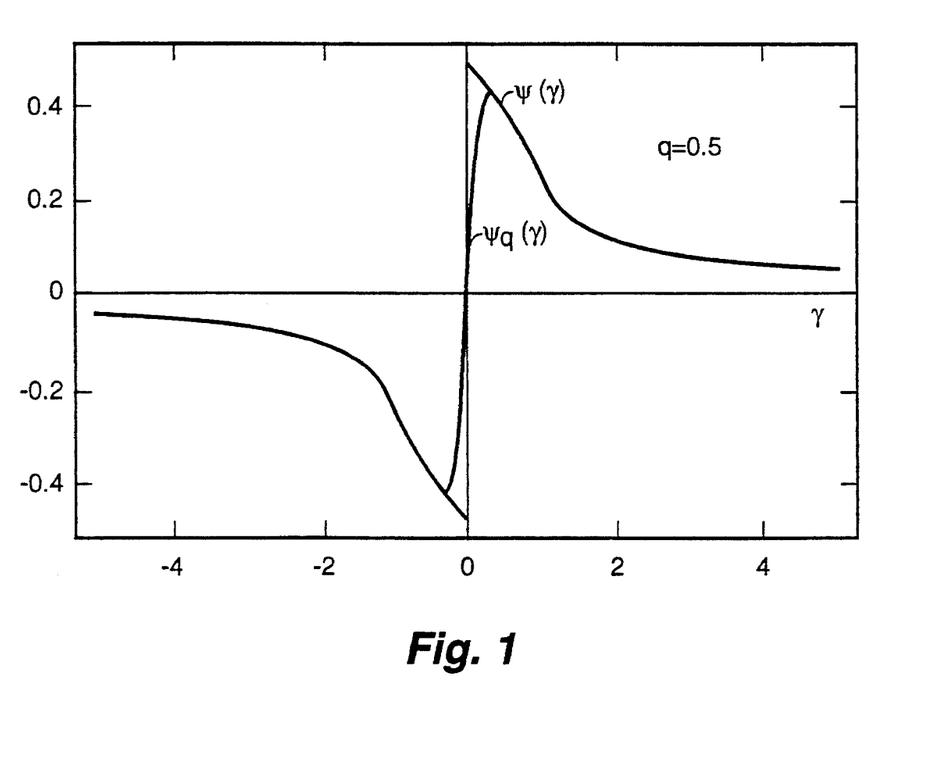
FIG. 1 is a graphical representation of the functions $\psi(\gamma)$ and $\psi_q(\gamma)$ for q=0.5.
Figure 2:
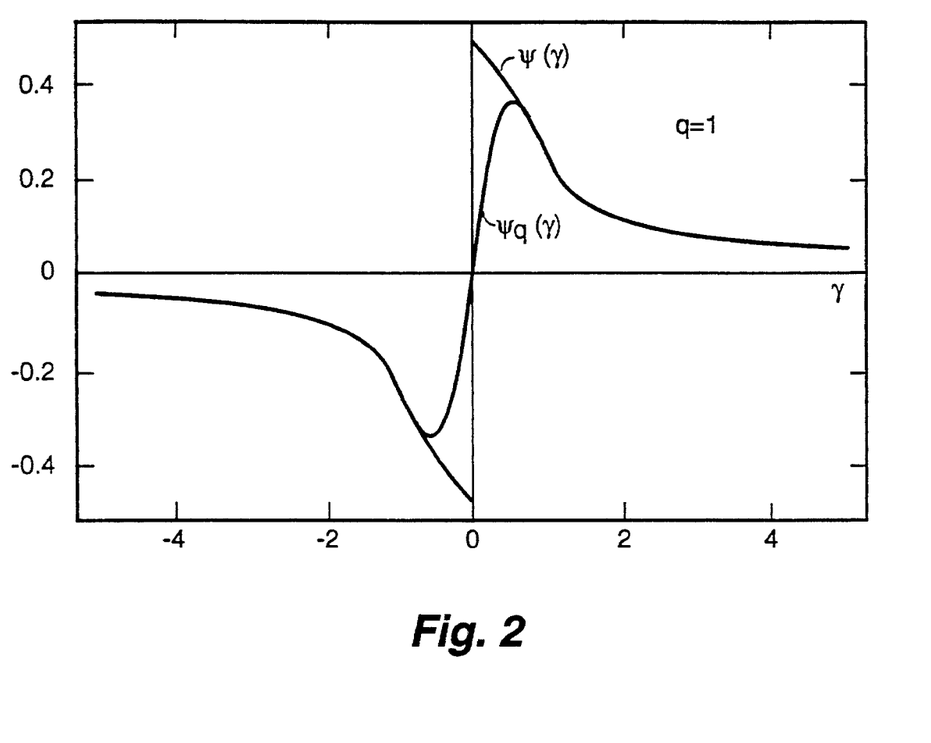
FIG. 2 is a graphical representation of the functions $\psi(\gamma)$ and $\psi_q(\gamma)$ for q=1.
Figure 3:
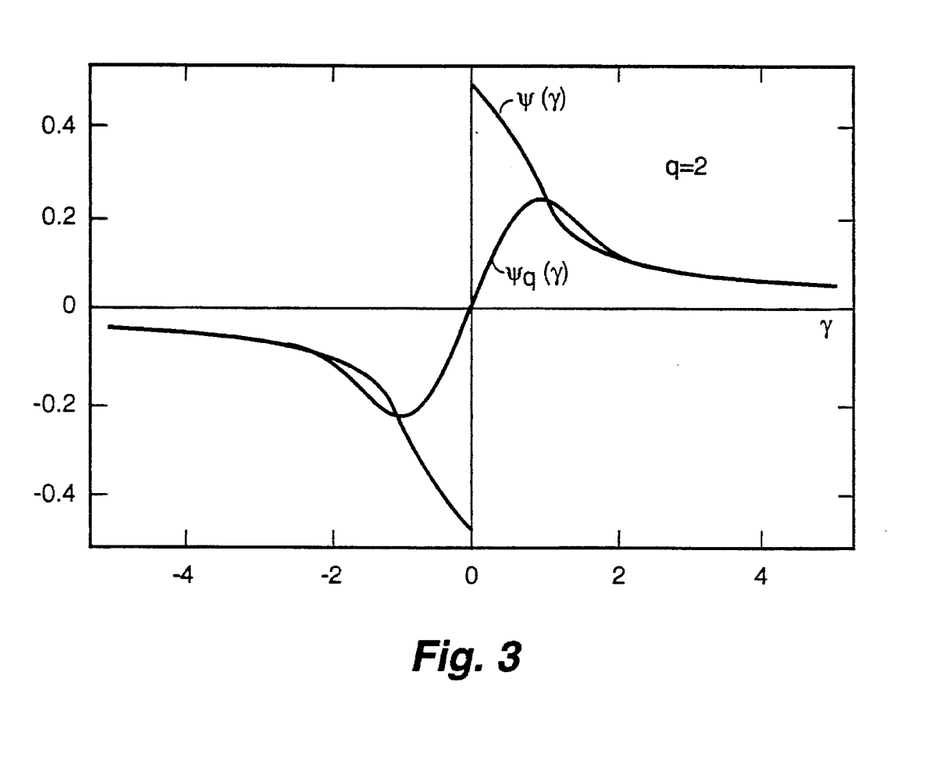
FIG. 3 is a graphical representation of the functions $\psi(\gamma)$ and $\psi_q(\gamma)$ for q=2.

Graphs of functions $\psi(\gamma)$ and $\psi_q(\gamma)$ for $\epsilon/d = q = 0.5, 1, 2$, are presented in FIGS. 1, 2, and 3, respectively. Corresponding values of $\gamma_0$ and $2\psi_q(\gamma_0)$ are $\gamma_0=0.33$, $2\psi_{0.5}(\gamma_0)=0.84$; $\gamma_0=0.56$, $2\psi_1(\gamma_0)=0.71$; $\gamma_0=0.91$, $2\psi_2(\gamma_0)=0.46$. Here, and in the numerical experiments described below, the following mollifier was used:

$$W_1(x) = \frac{m+1}{\pi} (1 - |x|^2)^m, m = 4. \quad \text{Eq. (9)}$$

From FIGS. 1–3, it may be seen that the smaller the ratio $q=\epsilon/d$ is, the better becomes the resolution of the pseudolocal tomography. If $\epsilon>0$ is fixed, d must be increased with a concomitant increase in the number of arithmetic operations per a discrete convolution $\omega_\epsilon(s)*\hat{f}(\theta,s)$ over the s-variable. Thus, the value of the ratio $q=\epsilon/d$ should be chosen as a trade-off between the desired resolution power and the speed of the algorithm.

Using the presented analysis, a process for finding the location and values of jumps using the PLT concept is as follows:

1. Fix a point $x_{i_0j_0}$ and assume that $x_{i_0j_0}$ belongs to $\Gamma$.
2. If $x_{i_0j_0}\in\Gamma$, find local maximum and local minimum of $f_{d\epsilon}$ in the neighborhood of $x_{i_0j_0}$.
3. Compute the estimate $|D(x_{i_0j_0})|$ according to Eq. (8). If $x_{i_0j_0}$ does not belong to $\Gamma$, the estimated values of $|D(x_{i_0j_0})|$ will be very small. If $x_{i_0j_0}$ belongs to $\Gamma$, the estimated values of $|D(x_{i_0j_0})|$ will be nonzero and will coincide with true jump values.

Many different schemes for numerical implementation of the above process are possible. An exemplary method follows:

Let the function $f_{d\epsilon}(X)$ be computed at the nodes of a square grid $x_{ij}=(ih,jh)$:

1. Fix a point $x_{i_0j_0}$ and consider, e.g., a 3×3 window around it, more particularly, consider the points $x_{ij}$, $|i-i_0|\leq 1$, $|j-j_0|\leq 1$.
2. Arrange the values $f_{d\epsilon}(x_{ij})$, $|i-i_0|\leq 1$, $|j-j_0|\leq 1$, in ascending order to get, e.g., a sequence of numbers $f_1\leq f_2\leq \ldots \leq f_9$.
3. Compute $\Phi(x_{i_0j_0})$ as the average value of the difference between the sum of the values $f_{d\epsilon}(x_{ij})$ on opposite sides of $\Gamma$, e.g., $|(f_7+f_8+f_9)-(f_1+f_2+f_3)|/3$.

In the algorithm, assume that h is sufficiently small or $\Gamma$ is sufficiently flat so that, if $x_{i_0j_0}\in\Gamma$, then f attains values, e.g., $f_1$, $f_2$, $f_3$ and $f_7$, $f_8$, $f_9$, on different sides of $\Gamma$.

Figure 4:
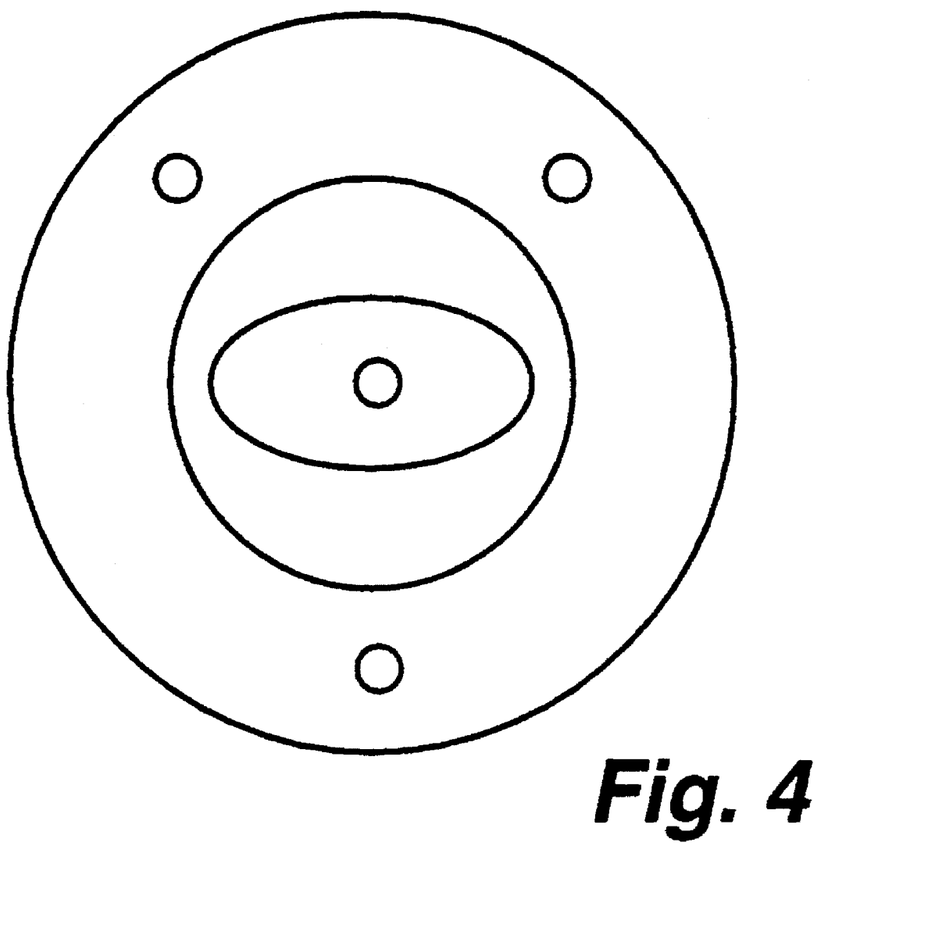
FIG. 4 illustrates an exemplary phantom for generating Radon transform data.

FIG. 4 illustrates an exemplary phantom for generating the Radon transform data. The densities are: exterior: 0, ellipse: 0.221, exterior annulus: 0.184, area between the annulus and the ellipse: 0.195, four small circles: 0.195. The Radon transform was computed for 250 angles equispaced on $[0, \pi]$ and 401 projections for each angle.

The density plot of the function $f_{d\epsilon}$ corresponding to the FIG. 4 phantom was computed at the nodes of a square 201×201 grid with parameters $d=6\Delta p$, $\epsilon=3\Delta p$, where $\Delta p$ is the discretization step of the p-variable. Thus, $q=\epsilon/d=0.5$. These values of d and $\epsilon$ mean that the discrete convolutions were computed using 19 points per integral. The grid step size was $h=2\Delta p$, so the condition $h_{opt}>\gamma_0 d$ was satisfied: $h=2\Delta p\geq 0.33\cdot 6\Delta p=1.98\Delta p$.

Figure 5:
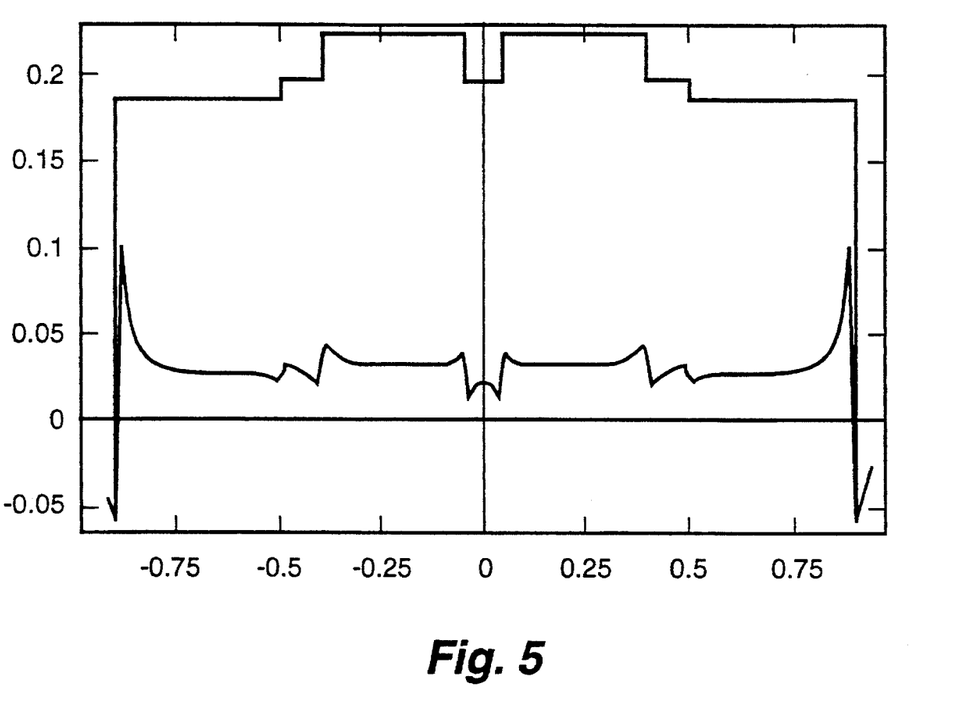
FIG. 5 is a horizontal cross-section of the density plot through the phantom shown in FIG. 4.
Figure 6:
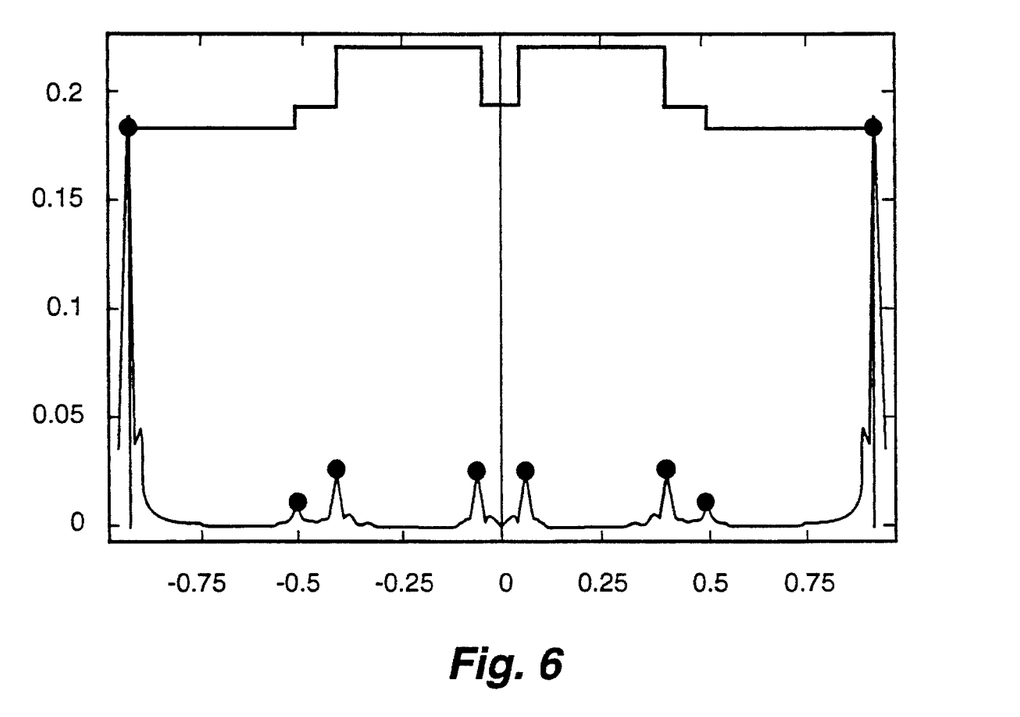
FIG. 6 is a horizontal cross-section of the values represented by FIG. 6.

The horizontal cross-section of the density plot is represented by FIG. 5. A piecewise constant function is a graph of $f(x)$, i.e., of the exact density, and the second line is a graph of $f_{d\epsilon}$. In FIG. 6, the horizontal cross-section density plot of the function $\Phi(x)/(2\psi_{0.5}(\gamma_0))$ is shown. The true jump values do not differ from the estimated ones by more than 5–6%. Big dots represent positions and amplitudes of jumps of the original density function f (the upper graph). There is very good agreement between the dots and the maxima of the peaks shown on FIG. 5.

The use of a pseudolocal tomography function $f_{\sigma d}$ for finding values of jumps of f requires investigation of the properties of $f_{\sigma d}$ as $x\to\Gamma$. In the first embodiment, $\sigma_d(p)=1$, $|p|\leq d$. However, this analysis depends on the cut-off function $\sigma_d(p)$ and, therefore, it should be done for each function $\sigma_d(p)$ separately.

The behavior of $f_{\sigma d}$, $x\to\Gamma$, can be obtained in an alternate manner. Indeed, assuming $d>0$ is sufficiently small so that $\Gamma$ can be considered flat inside d-neighborhood of $x_0$: $n_+=n_+(x_s)=n_+(x_0)$, $|x_s-x_0|\leq d$, $x_s$, $x_0\in\Gamma$ and, using the relationship $f_{\sigma d}=M_{\sigma d}*f\Lambda$, where $M_{\sigma d}$ is a function whose Radon transform $\hat{M}_{\sigma d}$ satisfies the relationship $$\hat{M'}_{\sigma d}(p) = -\frac{\sigma_d(p)}{\pi p}, |p|\leq d, \hat{M}_{\sigma d}(-d)=\hat{M}_{\sigma d}(d)=0, \quad \text{Eq. (12)}$$

and the function $f\Lambda$ is defined as follows:

$f\Lambda=F^{-1}(|\xi|Ff)$, where F and $F^{-1}$ are direct and inverse Fourier transforms, respectively.

The value $D(x_s)$ at $x_s\in\Gamma$ is proportional to the rate of change of the PLT function $f_{\sigma d,\epsilon}$ at $x_s$. This relationship is $$-\frac{\partial}{\partial h}f_{\sigma d,\epsilon}(x_s+hn_+)\bigg|_{h=0} = \quad \text{Eq. (13)}$$

$$\frac{D(x_s)}{\epsilon\pi^2}\int_{-1}^{+1}w_1(r)\int_{r-q}^{r+q}\frac{\sigma_q(r-t)}{r-t}((\epsilon t)^{-1}+c_2(x_s)\text{sign}(t)+c_3(x_s,t)dtdr,)$$

$q = d/\epsilon$

Now choose functions $w_1(r)$ and $\sigma_q(r)$ so that $$A_{\sigma q} = \int_{-1}^{1}w_1(r)\int_{r-q}^{r+q}\frac{\sigma_q(r-t)}{(r-t)t}dtdr \neq 0. \quad \text{Eq. (14)}$$

Then, $$-\frac{\partial}{\partial h}f_{\sigma d,\epsilon}(x_s+hn_+)\bigg|_{h=0} = \quad \text{Eq. (15)}$$

$$\frac{D(x_r)}{\epsilon\pi^2}A_{\sigma q}(1+O(\epsilon)), d=q\epsilon, \epsilon\to 0.$$

Use Eq. (2) to compute $f_{\sigma d}$, $$f_{\sigma d,\epsilon}(x) = \frac{1}{4\pi^2}\int_{S^1}\int_{\Theta\cdot x-(d+\epsilon)}^{\Theta\cdot x+(d+\epsilon)}w_{\sigma d,\epsilon}(\Theta\cdot x-p)\hat{f}(\theta,p)dpd\theta, \quad \text{Eq. (16)}$$

$$w_{\sigma d,\epsilon}(s) = \int_{s-d}^{s+d}\frac{\sigma_d(s-p)}{(s-p)}w'_\epsilon(p)dp$$

Neglecting the variation of $f_{\sigma d,\epsilon}(x_s+hn_+)$ with respect to $x_s$, $|\nabla f_{\sigma d,\epsilon}(x_0)|\approx\frac{\partial}{\partial h}f_{\sigma d,\epsilon}(x_0+hn_+)$, $x_0\in\Gamma$.

The values of jumps of f, i.e., density discontinuities, are determined using the following steps:

(0) Before processing the actual tomographic data, determine the constant $A_{\sigma q}$ according to Eq. (14);
(1) Determine $\nabla f_{\sigma d,\epsilon}(x)$ at the grid nodes (defined for the first process, above) $x=x_{ij}$ using the relationships $$g(s,\theta) = \int_{s-(d+\epsilon)}^{s+(d+\epsilon)} w'_{\sigma d,\epsilon}(s-p)\hat{f}(\theta,p)dp,$$

$$\frac{\partial f_{\sigma d,\epsilon}(x)}{\partial x_1} = \frac{1}{4\pi^2} \int_{S^1} \cos(\theta)g(\Theta \cdot x, \theta)d\theta,$$

$$\frac{\partial f_{\sigma d,\epsilon}(x)}{\partial x_2} = \frac{1}{4\pi^2} \int_{S^1} \sin(\theta)g(\Theta \cdot x, \theta)d\theta;$$

(2) Determine the estimate of the discontinuity $|D(x_{ij})|$ from Eq. (15);

(3) The vector $\nabla f_{\sigma d,\epsilon}(x_{ij})$ points from the smaller values of f to the larger values of f.

Figure 7:
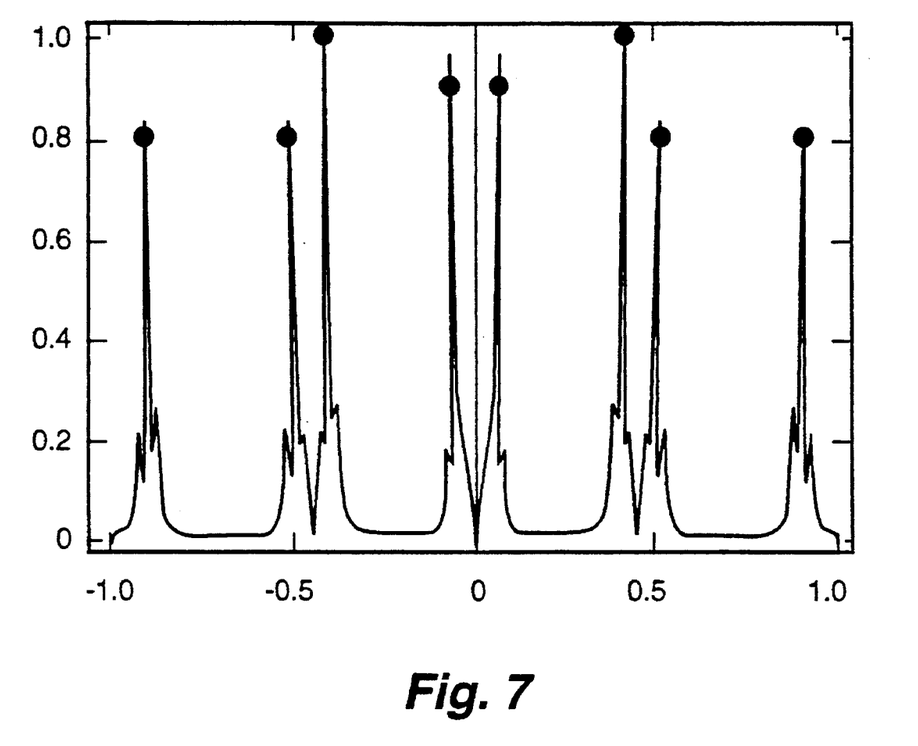
FIG. 7 is a horizontal cross-section of the density values determined by a second embodiment of the present invention.

A phantom, similar to the one shown in FIG. 4, was used for generating Radon transform data with densities of: exterior: 0, ellipse: 1, exterior annulus: 0.8, area between the annulus and the ellipse: 0, three small disks off the center: 1.8, small center disk: 0.1. The horizontal cross-section of the density plot of the estimated $|D(x)|$ is shown in FIG. 7. In the determinations, mollifer $W_\epsilon$ was selected as $$W_1(x) = \frac{m+1}{\pi}(1-|x|^2)^m$$

m=8, with $\epsilon=9\Delta p$, and the cut-off function $\sigma_d(p)=(1-(p/d)^4)^4$, $d=10\Delta p$. Thus, $q=d/\epsilon \approx 1.1$. Again $\Delta p$ is the discretization step in the p-variable.

As shown in FIG. 7, the values of discontinuities estimated using the PLT approach (smooth line) do not differ from the actual discontinuity values (dots) by more than 5–6% in value and the peaks are located at the actual locations.

It will be understood that the above analysis is directed to attenuation data obtained from a parallel beam protocol. But the invention is not limited to parallel beam protocols. Indeed, other protocols, such as a fan beam protocol (all of the attenuation paths originate from a common source and the common sources are angularly spaced) can be converted to a parallel beam protocol by conventional geometric conversions. For example, the conversion from a fan beam to a parallel beam uses the rotation matrix:

$$R_\alpha x = \begin{pmatrix} x_1\cos\alpha + x_2\sin\alpha \\ -x_1\sin\alpha + x_2\cos\alpha \end{pmatrix},$$

such that for $\theta,p$: $\theta \in (0,2\pi), |p| \leq a$, the fan beam is characterized by $\phi, \alpha$ so that $\sin\phi=p/a, \alpha=\phi+\pi/2-\theta(\mathrm{mod}\,2\pi)$. Thus, the same process may be used for both parallel beam and fan beam protocols with conventional mathematical processing.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for determining by tomography the location and value of a discontinuity between a first internal density of an object and a second density of a region within said object, comprising the steps of:

directing a beam of radiation in a predetermined pattern through said region of said object containing said discontinuity;

determining relative attenuation data of said beam within said predetermined pattern having a first data component that includes attenuation data through said region;

inputting said relative attenuation data to a pseudo-local tomography function, where the difference between said first internal density and said pseudo-local tomography function is continuous everywhere and said pseudo-local tomography function is computed across said discontinuity; and outputting from said pseudo-local tomography function the location of said discontinuity and the difference in density between said first density and said second density.

2. A method according to claim 1, wherein said pseudo-local tomography function is $$f_{\sigma d}(x) = \frac{1}{4\pi^2} \int_{S^1} \int_{x\cdot\Theta - d}^{x\cdot\Theta + d} \frac{\sigma_d(x\cdot\Theta - p)\hat{f}(\theta,p)}{x\cdot\Theta - p} \, dp\,d\theta,$$

where $x \in \mathfrak{R}^2$, so that the function $f_{\sigma d}(x)$ is computed at a point x using $\hat{f}(\theta,p)$ for $(\theta,p)$ satisfying $|\Theta\cdot x - p| \leq d$, wherein integrals of f are taken along only lines passing at a distance not exceeding d from the point x.

3. A method according to claim 2, wherein $\sigma_d = 1$ and $$f_d(x) = \frac{1}{4\pi^2} \int_{S^1} \int_{x\cdot\Theta - d}^{x\cdot\Theta + d} \frac{\hat{f}(\theta,p)}{x\cdot\Theta - p} \, dp\,d\theta,$$

where $x \in \mathfrak{R}^2$.

4. A method according to claim 3, wherein the step of outputting the location of said discontinuity and the difference in density includes the steps of:

computing at nodes of a grid $(x_{ij})=(ih,jh)$ around the function $$f_{d\epsilon} = (f_d * W_\epsilon) = \frac{1}{4\pi^2} \int_{S_1} \int_{x\cdot\Theta - d - \epsilon}^{x\cdot\Theta + d + \epsilon} \tilde{w}_\epsilon(x\cdot\Theta - s)\hat{f}(\theta,s)ds\,d\theta,$$

where $$\tilde{w}_\epsilon(s) = \int_{s-d}^{s+d} \frac{w'_\epsilon(p)}{s-p} dp,$$

and $$w'_\epsilon(p) = 2p \int_p^\epsilon \frac{W_\epsilon(r)}{\sqrt{r^2-p^2}} dr,$$

$0 \leq p \leq \epsilon', w'_\epsilon(-p) = -w'_\epsilon(p), p > 0, w'_\epsilon(p) = 0, |p| \geq \epsilon$ arrange the values of $f_{d\epsilon}$ is ascending order to define a sequence of values;

compute $\Phi(x_{i_0 j_0})$ as the difference between values of local maximum and local minimum of $f_{d\epsilon}$; occurring in the neighborhood of $x_{i_0 j_0}$;

normalize $\Phi(x_0)$; and locate maxima of $\Phi(x_0)$ to output the location and value of said discontinuity between said first internal density of said object and said second density of said region within said object.

5. A method according to claim 2, further including the steps of determining the constant $$A_{\sigma q} = \int_{-1}^{1} w_1(r) \int_{r-q}^{r+q} \frac{\sigma_q(r-t)}{(r-t)t} \, dt dr \neq 0:$$

determining a gradient $\nabla f_{\sigma d,\epsilon}(x)$ related to the attenuation coefficient f at grid points located on opposite sides of said location of said density discontinuity;

determining said value of said density discontinuity from said gradient.

* * * * *